United States Patent [19]
Thornton

[11] Patent Number: 5,546,956
[45] Date of Patent: Aug. 20, 1996

[54] TESTING HEARING

[75] Inventor: Arthur R. D. Thornton, Southampton, United Kingdom

[73] Assignee: Medical Research Council, London, United Kingdom

[21] Appl. No.: 313,212

[22] PCT Filed: Mar. 29, 1993

[86] PCT No.: PCT/GB93/00639

§ 371 Date: Feb. 13, 1995

§ 102(e) Date: Feb. 13, 1995

[87] PCT Pub. No.: WO93/19670

PCT Pub. Date: Oct. 14, 1993

[51] Int. Cl.$^6$ ........................................ A61B 5/00
[52] U.S. Cl. ............................................... 128/746
[58] Field of Search ................................ 128/739, 740, 128/746, 897, 898

[56] References Cited

FOREIGN PATENT DOCUMENTS 7900614  9/1979  WIPO.

OTHER PUBLICATIONS

Burkard et al. "A Comparison of Max. Length & Legendre Sequences . . . " J. Acoust Soc. Am. 87(4) Apr. 1990 pp. 1656–1664.

Shi et al., "The use of M pulse sequences . . . " IEEE Engin. Con. Nov. 1989.

Avan et al., "Quantitative assessment . . . emissios" Hearing Research 52 1991 pp. 99–112.

Eysholdt et al., "Maximum Length Sequence . . . Responses", Audiology 21 1982 pp. 242–250.

*Primary Examiner*—Max Hindenburg
*Attorney, Agent, or Firm*—Lee, Mann, Smith, McWilliams, Sweeney & Ohlson

[57] ABSTRACT

An apparatus for testing hearing comprises a sound source for applying a sound to the subject's ear and a sound detector for detecting the sound returned from the subject's inner ear in response to the sound. The sound source, which is driven by stimulus generation equipment connected to an analyzer, produces a sequence of sounds constituting a maximum length sequence to record Evoked Otocoustic Emissions.

10 Claims, 6 Drawing Sheets

A SCHEMATIC DIAGRAM OF THE INVENTION

FIGURE 1: A SCHEMATIC DIAGRAM OF THE INVENTION
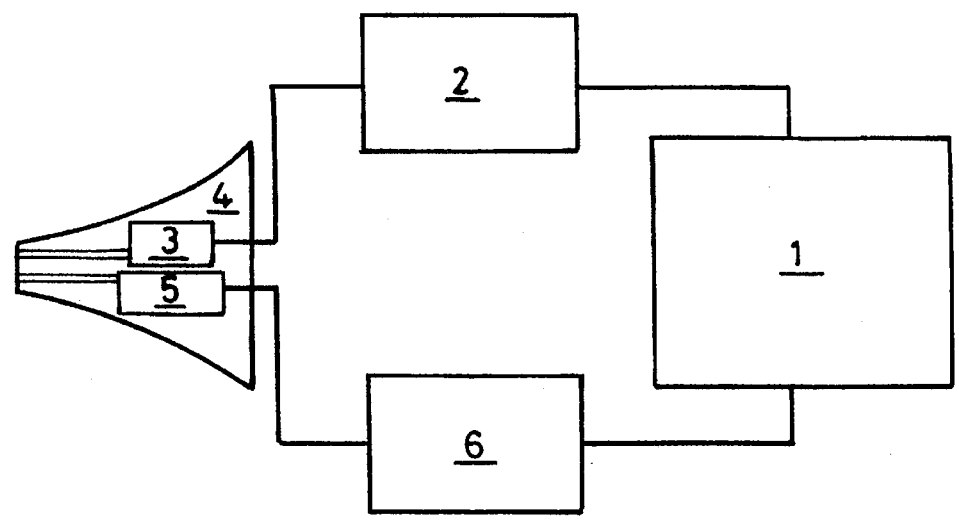

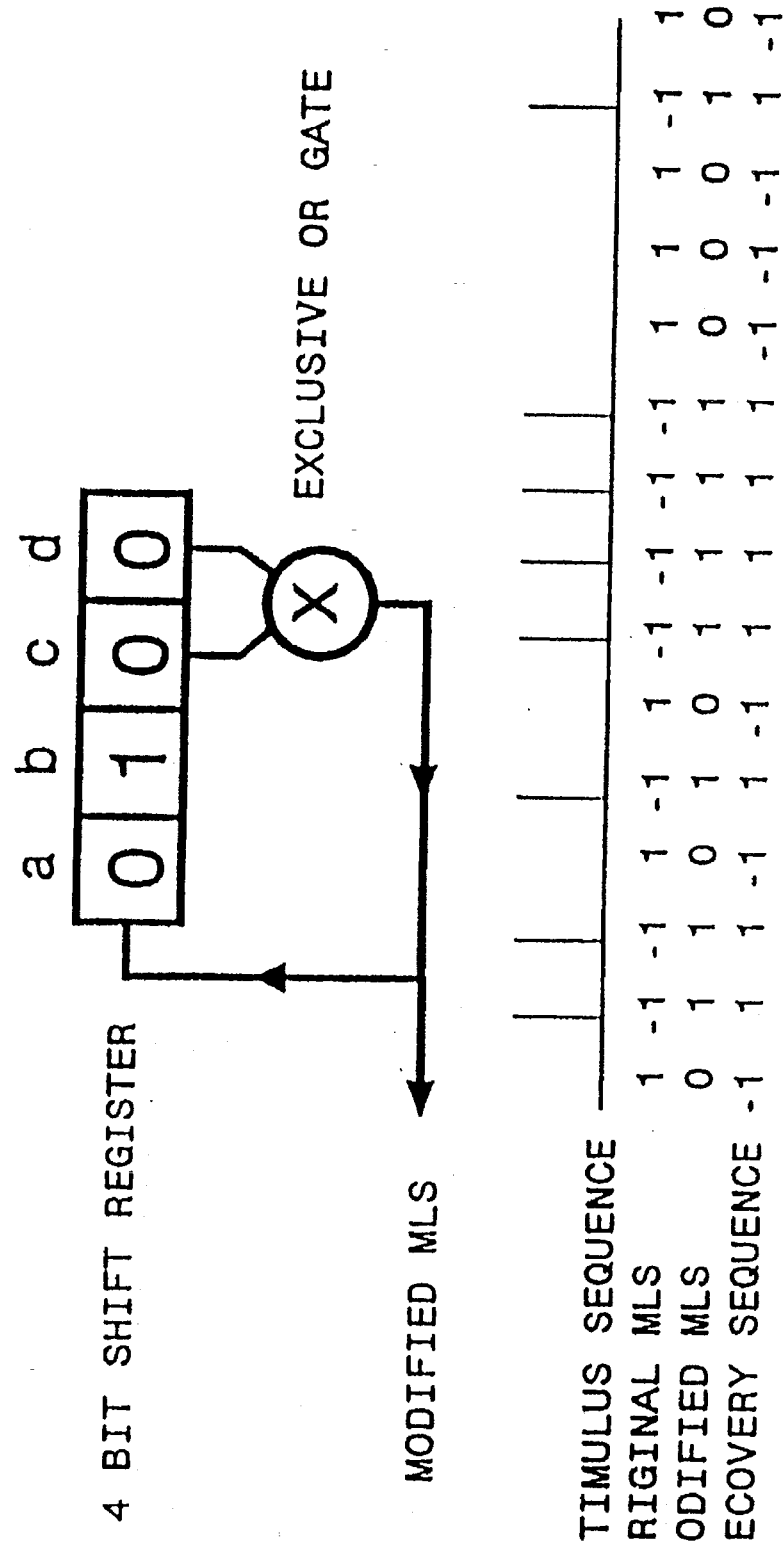
FIGURE 2: AN EXAMPLE OF AN MLS STIMULUS SEQUENCE

FIGURE 3: DECONVOLUTION AND RECOVERY PROCEDURES

A $$\begin{bmatrix} 1 & 0 & 0 & 1 & 0 & 1 & 1 \\ 0 & 0 & 1 & 0 & 1 & 1 & 1 \\ 0 & 1 & 0 & 1 & 1 & 1 & 0 \\ 1 & 0 & 1 & 1 & 1 & 0 & 0 \\ 0 & 1 & 1 & 1 & 0 & 0 & 1 \\ 1 & 1 & 1 & 0 & 0 & 1 & 0 \\ 1 & 1 & 0 & 0 & 1 & 0 & 1 \end{bmatrix} \times \begin{bmatrix} 1 \\ -1 \\ -1 \\ 1 \\ -1 \\ 1 \\ 1 \end{bmatrix} = \begin{bmatrix} 1 & 0 & 0 & 1 & 0 & 1 & 1 \\ 0 & 0 & -1 & 0 & -1 & -1 & -1 \\ 0 & -1 & 0 & -1 & -1 & -1 & 0 \\ 1 & 0 & 1 & 1 & 1 & 0 & 0 \\ 0 & -1 & -1 & -1 & 0 & 0 & -1 \\ 1 & 1 & 1 & 0 & 0 & 1 & 0 \\ 1 & 1 & 0 & 0 & 1 & 0 & 1 \end{bmatrix}$$

SUM= 4 0 0 0 0 0 0

B $$\begin{bmatrix} 1 & -1 & -1 & 1 & -1 & 1 & 1 \\ -1 & -1 & 1 & -1 & 1 & 1 & 1 \\ -1 & 1 & -1 & 1 & 1 & 1 & -1 \\ 1 & -1 & 1 & 1 & 1 & -1 & -1 \\ -1 & 1 & 1 & 1 & -1 & -1 & 1 \\ 1 & 1 & 1 & -1 & -1 & 1 & -1 \\ 1 & 1 & -1 & -1 & 1 & -1 & 1 \end{bmatrix} \times \begin{bmatrix} 1 \\ 0 \\ 0 \\ 1 \\ 0 \\ 1 \\ 1 \end{bmatrix} = \begin{bmatrix} 1 & -1 & -1 & 1 & -1 & 1 & 1 \\ 0 & 0 & 0 & 0 & 0 & 0 & 0 \\ 0 & 0 & 0 & 0 & 0 & 0 & 0 \\ 1 & -1 & 1 & 1 & 1 & -1 & -1 \\ 0 & 0 & 0 & 0 & 0 & 0 & 0 \\ 1 & 1 & 1 & -1 & -1 & 1 & -1 \\ 1 & 1 & -1 & -1 & 1 & -1 & 1 \end{bmatrix}$$

SUM= 4 0 0 0 0 0 0

C $$\begin{bmatrix} 1 & -1 & -1 & 1 & -1 & 1 & 1 \\ -1 & -1 & 1 & -1 & 1 & 1 & 1 \\ -1 & 1 & -1 & 1 & 1 & 1 & -1 \\ 1 & -1 & 1 & 1 & 1 & -1 & -1 \\ -1 & 1 & 1 & 1 & -1 & -1 & 1 \\ 1 & 1 & 1 & -1 & -1 & 1 & -1 \\ 1 & 1 & -1 & -1 & 1 & -1 & 1 \end{bmatrix} \times \begin{bmatrix} 1 \\ -1 \\ -1 \\ 1 \\ -1 \\ 1 \\ 1 \end{bmatrix} = \begin{bmatrix} 1 & -1 & -1 & 1 & -1 & 1 & 1 \\ 1 & 1 & -1 & 1 & -1 & -1 & -1 \\ 1 & -1 & 1 & -1 & -1 & -1 & 1 \\ 1 & -1 & 1 & 1 & 1 & -1 & -1 \\ 1 & -1 & -1 & -1 & 1 & 1 & -1 \\ 1 & 1 & 1 & -1 & -1 & 1 & -1 \\ 1 & 1 & -1 & -1 & 1 & -1 & 1 \end{bmatrix}$$

SUM= 7 -1 -1 -1 -1 -1 -1

POSITIVE CLICK RUN: 1 1 1 1 1 1 1

TOTAL: 8 0 0 0 0 0 0

FIGURE 4: A VARIANT OF THE NORMAL MLS AND THE RECOVERY PROCEDURE

FIGURE 5: PROBE WITH AN ARRAY OF TWO MICROPHONES
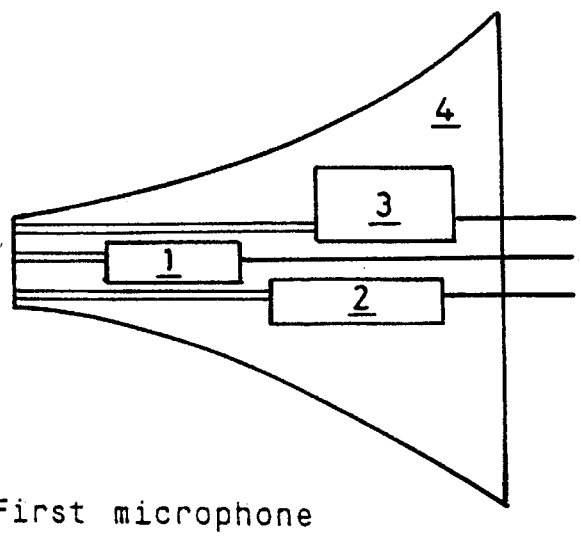
1: First microphone
2: Second microphone
3: Loudspeaker
4: Probe

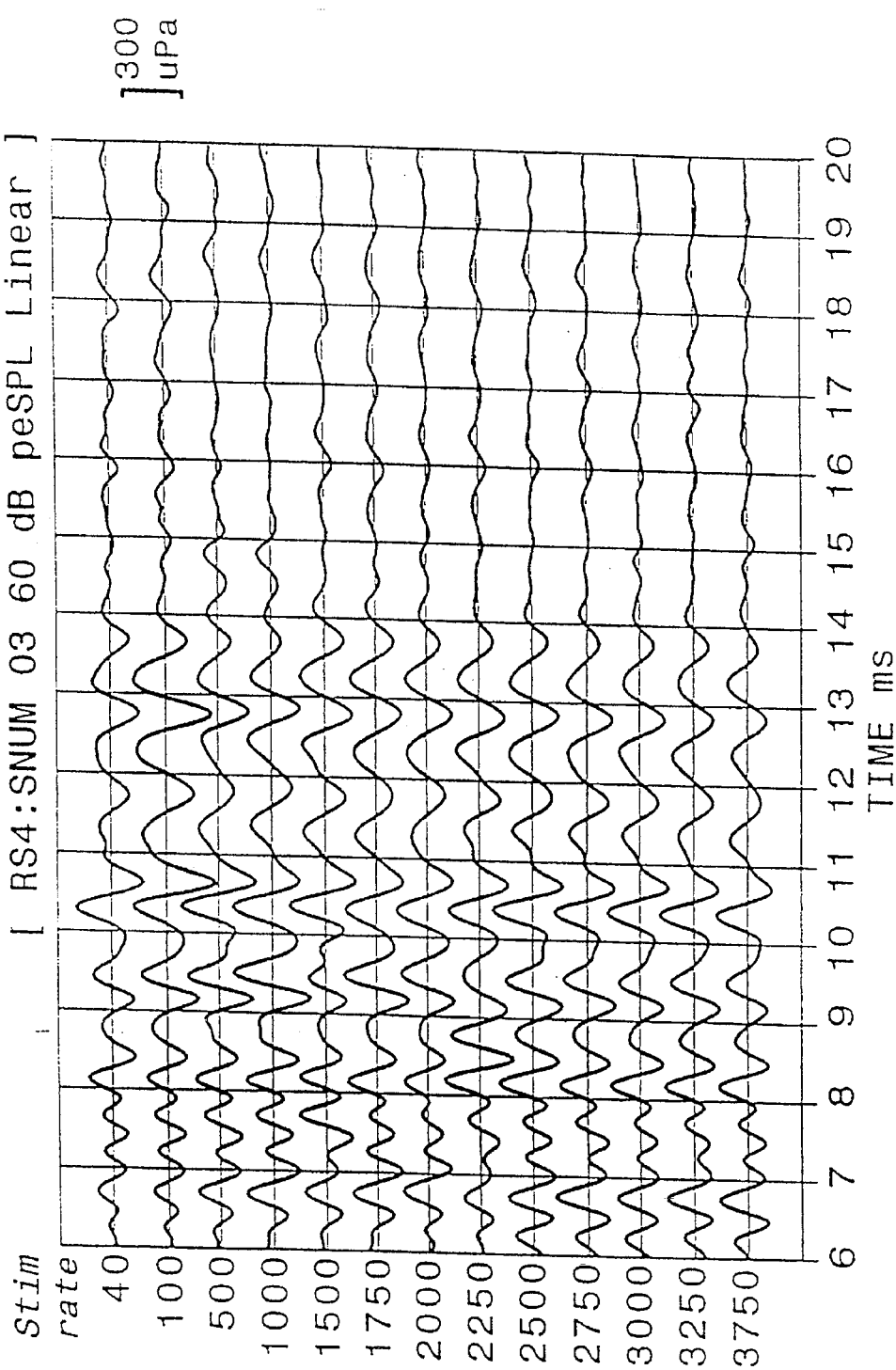
FIGURE 6: AN EXAMPLE OF CONVENTIONAL AND MLS RECORDINGS OF EVOKED OTOACOUSTIC EMISSIONS FROM A NORMALLY HEARING SUBJECT

TESTING HEARING

FIELD OF THE INVENTION

This invention relates to apparatus for, and a method of, testing hearing.

BACKGROUND TO THE INVENTION

EP 0015258 discloses hearing faculty testing apparatus comprising an aural probe for insertion into a subject's external ear canal. The probe includes an electroacoustic transducer for projecting sound into the ear canal and for responding to sound waves returned from the inner ear in response to the projected sound. The transducer is energised by a pulse generator which is said to have a maximum useful frequency of about 50 Hz, because at higher frequencies the echoes overlap with succeeding pulses. Throughout, this prior patent specification refers to extracting echoes by electronic time gating. The need to avoid overlapping and to extract the echoes by time gating represents a disadvantage which the present invention aims to overcome.

DISCLOSURE OF THE INVENTION

According to one aspect of the invention apparatus for testing hearing comprises a sound source for applying a sound to a subject's ear and a sound detector for detecting the sound returned from the subject's inner ear in response to said sound, characterised in that said sound source produces a sequence of sounds constituting a maximum length sequence (MLS), a variant of such a sequence or a variant of a similar sequence. Possible variants are Legendre sequences, M-pulse sequences and De Bruijn sequences.

According to another aspect of the invention there is provided a method of testing hearing, wherein sound is applied to a subject's ear and the sound reflected from the subject's inner ear is detected, characterised in that the sound sequence constitutes a maximum length sequence (MLS), a variant of such a sequence or a variant of a similar sequence. The invention thus resides in the use of a maximum length sequence (or similar sequence) to record Evoked Otoacoustic Emissions (EOAEs). The invention uses stimulation at rates higher than 50 Hz.

Two sequences may be used simultaneously and two ears may be tested simultaneously.

EOAEs are acoustic signals produced by the motile cochlear hair cells in response to the input stimulus and transmitted through the middle ear space to the external acoustic meatus where they can be recorded using a microphone. EOAEs are like fingerprints and vary markedly between ears and individuals but are remarkably stable within an individual.

A maximum length sequence (MLS) is a quasi-random binary sequence with strictly defined mathematical properties. The MLS is a pseudorandom binary (or multi level sequence) x(n) periodic with period p, having the property that $$\sum_{n=1}^{p} x(n)x(n+t) = \begin{cases} a & \text{if } t = 0 \text{ or some integer multiple of } p \\ b & \text{otherwise,} \end{cases}$$

where a and b are constants. In other words, the sequence's autocorrelation function is two valued. Various techniques, such as shift registers, can be employed to produce such sequences which include maximum length sequences (also called PN sequences and m-sequences) and Legendre sequences.

The original work on these sequences was carried out in the field of radar but, since then, they have been applied to the recording of electrical evoked potentials (Eysholdt, U and Schreiner, Chr., 1982).

The invention enables this technique to be used to record otoacoustic evoked emissions.

The property of MLSs that makes them of interest and applicability is the fact that in order to record a response of say 20 ms duration, the time between the stimuli used to obtain this response can be considerably less than the response itself. Thus by recourse to the invention it is possible to stimulate at a rate of 500 or more clicks a second, instead of stimulating at less than 50 clicks a second. In this way, a sufficient number of responses is obtained that will produce a clear average waveform in very much less than the normal test time. The responses overlap each other and, if normal stimulation were applied at such a rate, the waveform would be the product of the overlapped responses and would be worthless. However, if a MLS is used the original response can be recovered from the overlapped, averaged waveform.

This technique is particularly suitable for evoked emissions as they do not adapt to fast rates of stimulation in the same way that the auditory brainstem response does. Thus, this is different in essence from the published work using MLS with auditory brainstem response.

The applications of the inventive technique are in audiological and neurological diagnosis but a principal application is in neonatal screening where evoked otoacoustic emissions (EOAEs) have their major clinical application. It should be possible, using this technique, to test a baby's hearing with a measurement lasting no more than a second or so. This leads to the possibilities of hand-held probes and a very quick and efficient system for testing newborn babies, as well as the possibility of getting usable measurements from a very brief presentation to older uncooperative children.

Apparatus for testing hearing and forming a preferred embodiment of the invention will now be described, by way of example, with reference to the accompanying drawings, in which:

FIG. 1 is a schematic diagram of the apparatus,

FIG. 2 illustrates an example of an MLS stimulus sequence,

FIG. 3 illustrate a deconvolution and recovery procedure,

FIG. 4 illustrates a variant of the preferred MLS and the recovery procedure,

FIG. 5 illustrates a probe with two microphones, and

FIG. 6 shows an example of otoacoustic emissions.

FIG. 1 shows a schematic diagram of the preferred apparatus. The apparatus comprises an analyser 1 which may be a computer, microprocessor or other apparatus used to perform the averaging, deconvolution and other analytical and control functions. This is connected to and controls the stimulus generation equipment 2. The stimulus is fed to a small transducer 3 which feeds a sound wave into the ear canal of the person being tested, via a small probe 4 designed to fit into the ear canal. Within, or connected to the same probe, in the same way that is found in middle ear impedance measuring equipment, there is a small microphone 5 which conveys the sound recorded in the ear canal to signal-conditioning equipment 6 that may include pre-amplifiers, filters and amplifiers. The output from the equipment 6 is fed to the analyser.

The stimulus may comprise condensation and/or rarefaction clicks, tone-bursts or noise-bursts. In all that follows, for the sake of simplicity, stimuli comprising a series of clicks will be used to illustrate the method.

The clicks are presented according to the particular rules that govern a maximum length sequence. Mathematically, such a binary sequence is often expressed as the two values −1 and +1. For the purposes described here, this has been transformed in the following manner. All occurrences of −1 are replaced by +1 and all occurrences of +1 are replaced by 0. The value 1 then represents the presentation of a click and the value zero represents a silent interval in the click sequence.

One way of generating such a sequence is by the use of a shift register with an exclusive-or gate attached to two or more of the bits whose output is fed back to the entry of the shift register. FIG. 2 illustrates such a system which will produce a maximum length sequence of $2^n-1$ where n is the number of bits in the shift register. In this example n is 4 and we will have an MLS of length 15.

In recording small amplitude responses, such as the auditory brainstem response and evoked otoacoustic emissions, the response is generally too small to be distinguished from ambient and instrument noise. The signal-to-noise ratio is therefore usually enhanced by various techniques including time-domain and frequency-domain averaging. A certain number of responses are required to be fed into the averaging procedure in order to improve the signal-to-noise ratio by the required amount. The advantage of the MLS technique is that the minimum time between clicks can be much shorter than the duration of the response which is being measured. Thus, a sufficient number of responses can be obtained for the averaging procedure in a much shorter time.

However, as the time between clicks is less than the response duration, clearly the responses will overlap each other and the resultant, averaged waveform will not resemble the original response. Were a conventional stimulation sequence used this mixture of overlapped responses would be the end result and would not show the response in its normal form. However, with the MLS technique the original response may be recovered from the overlapped, averaged responses by using a deconvolution procedure.

One example of the practical implementation of such a procedure is as follows. Let the minimum time between stimuli be denoted by T and the averaged, overlapped response be denoted by O. The original response (R) may be recovered in the following manner.

A copy of the digitised waveform (O) is placed in a computer buffer memory and is denoted by OC. If the first element in the MLS sequence is a zero (or a silence) then the copy waveform (OC) is inverted (or multiplied by −1). The original waveform (O) is then rotated left by the number of samples that corresponds to the time interval T. This rotated waveform is then added to or subtracted from the copy (OC) in the buffer memory, dependent upon the value of the second element in the MLS, according to the rules established above. This procedure is repeated for the entire length of the MLS and, when it is complete, the original response R will be left in the buffer memory. This waveform may then be viewed on a screen, a hard copy made of it and it may be stored on various optical, electromagnetic etc, computer media.

FIG. 3 illustrates the deconvolution or recovery process. In 3A, the stimulus sequence is 1 0 0 1 0 1 1 and so the recovery sequence is 1 −1 −1 1 −1 1 1. The matrix at the left hand side is the stimulus sequence plus six copies of itself, each one rotated one place to the left, relative to the preceding sequence. The matrix in the middle is the recovery sequence and the one on the right hand side is the product of the two previous matrices. The sum of all the elements in the right hand matrix gives the recovered signal at 4 times its original amplitude (because there are 4 clicks in the MLS) and all other occurrences of stimulus and response are cancelled to zero. In 3B, bipolar stimulation is represented by the stimulus sequence 1 −1 −1 1 −1 1 1. This is the same as the previous sequence (3A) except that all occurrences of 0 have been replaced by −1. Such a sequence of condensation and rarefaction clicks can be delivered as described before. Having swapped 0s and −1ls in the stimulus sequence, the same has been done in the recovery sequence which now becomes 1 0 0 1 0 1 1 . If the operations described above are repeated then the same result is obtained.

A new variant is shown in FIG. 3C. Here the stimulus sequence in 3B has been combined with the recovery sequence of 3A. The result is a recovered signal of 7 times its original amplitude but with artefacts or unwanted components of amplitude =−1 at every stimulus opportunity position thereafter. However, if a sequence of positive clicks is given, with a click in every stimulus opportunity position, then, when this is added to the previous result, a properly recovered signal of 8 times the original amplitude is achieved. One practical way of implementing this technique is to sum an adequate number, say m, MLSs to obtain the required signal-to-noise ratio improvement then follow this by adding to the sum the responses elicited by m positive click runs. The advantage of this variant is that the recovered signal has twice the amplitude for approximately the same recording time, compared to the methods illustrated in 3A and 3B.

A more radical variant is shown in FIG. 4. Here, an MLS is generated followed by a negative click. Immediately following this a copy of the same MLS, rotated one place to the left, is generated, again followed by a negative click. This procedure is repeated until all distinct rotations of the MLS are complete. Then a sequence of negative clicks are used as the stimulus train. This is shown as the left hand matrix in FIG. 4. The recovery sequence, identical to that used in FIG. 3A and 3C, is used again with the addition of a negative click at the end. The recovered signal has double the amplitude that it would have using the methods illustrated in FIG. 3A and 3B.

Another means of improving the signal-to-noise ratio is shown in FIG. 5. Here, instead of using a single microphone an array of two or more microphones are used. The microphones are arranged at different distances from the eardrum. From a knowledge of the distance between the microphones, the time delay or phase difference in the signals coming from the ear is known. This enables the signals coming from the ear to be enhanced relative to those going in the opposite direction. Thus, the evoked emission will be recorded with less interference from external noise.

FIG. 6 shows an example of otoacoustic emissions recorded conventionally, at a click rate of 40 clicks/s, and with the inventive MLS technique at maximum rates from 100 to 3750 clicks/s. The conventional and MLS recorded emissions are very similar in appearance. Data from 10 normally hearing subjects have shown that the correlations between MLS emissions recorded at different stimulus rates are high and indicate very similar waveforms. Table I shows the mean correlation values obtained.

At very high stimulation rates, it may be that the stimulus transducer may alter its output because the recovery time between one stimulus and the next is not long enough. In such cases two transducers can be placed in the probe and alternate stimuli sent to each transducer. This will ensure that each transducer has at least twice the recovery time than it would have if only one transducer were used. This principle may be extended to any number of transducers.

Correlation matrix for linear components for conventional recordings
(rate = 40/s) and MLS recordings (rate = 100 to 3750/s).

Stimulus level: 60 dB

|  |  | Stimulus rate clicks/s | | | | | | | | | | | | |
|---|---|---|---|---|---|---|---|---|---|---|---|---|---|---|
|  |  | 40 | 99 | 499 | 999 | 1498 | 1763 | 1998 | 2305 | 2498 | 2725 | 2997 | 3330 | 3747 |
| stimulus | 40 | .96 | .94 | .91 | .91 | .83 | .85 | .88 | .91 | .90 | .89 | .88 | .87 | .87 |
| rate | 99 |  | .91 | .90 | .89 | .83 | .85 | .89 | .88 | .87 | .86 | .85 | .84 | .83 |
| clicks/s | 499 |  |  | .95 | .92 | .87 | .80 | .86 | .88 | .88 | .87 | .87 | .86 | .86 |
|  | 999 |  |  |  | .97 | .83 | .83 | .91 | .90 | .89 | .87 | .87 | .85 | .88 |
|  | 1498 |  |  |  |  | .97 | .84 | .83 | .87 | .87 | .87 | .88 | .87 | .86 |
|  | 1763 |  |  |  |  |  | .97 | .90 | .89 | .88 | .89 | .87 | .89 | .88 |
|  | 1998 |  |  |  |  |  |  | .98 | .91 | .90 | .90 | .90 | .89 | .90 |
|  | 2305 |  |  |  |  |  |  |  | .98 | .94 | .94 | .92 | .92 | .93 |
|  | 2498 |  |  |  |  |  |  |  |  | .98 | .95 | .94 | .94 | .94 |
|  | 2725 |  |  |  |  |  |  |  |  |  | .99 | .97 | .96 | .95 |
|  | 2997 |  |  |  |  |  |  |  |  |  |  | .98 | .96 | .96 |
|  | 3330 |  |  |  |  |  |  |  |  |  |  |  | .99 | .96 |
|  | 3747 |  |  |  |  |  |  |  |  |  |  |  |  | .99 |

Stimulus level: 70 dB

|  |  | stimulus rate clicks/s | | | | | | | | | | | | |
|---|---|---|---|---|---|---|---|---|---|---|---|---|---|---|
|  |  | 40 | 99 | 499 | 999 | 1498 | 1763 | 1998 | 2305 | 2498 | 2725 | 2997 | 3330 | 3747 |
| stimulus | 40 | .97 | .91 | .91 | .86 | .81 | .83 | .87 | .88 | .84 | .84 | .80 | .81 | .79 |
| rate | 99 |  | .92 | .85 | .82 | .78 | .82 | .85 | .83 | .82 | .82 | .81 | .83 | .80 |
| clicks/s | 499 |  |  | .98 | .92 | .86 | .84 | .89 | .88 | .86 | .88 | .84 | .83 | .83 |
|  | 999 |  |  |  | .97 | .80 | .83 | .89 | .87 | .84 | .86 | .86 | .81 | .85 |
|  | 1498 |  |  |  |  | .98 | .91 | .88 | .90 | .86 | .89 | .87 | .88 | .87 |
|  | 1763 |  |  |  |  |  | .98 | .92 | .93 | .91 | .92 | .90 | .92 | .91 |
|  | 1998 |  |  |  |  |  |  | .99 | .93 | .93 | .94 | .93 | .91 | .93 |
|  | 2305 |  |  |  |  |  |  |  | .99 | .93 | .94 | .91 | .93 | .91 |
|  | 2498 |  |  |  |  |  |  |  |  | .99 | .96 | .94 | .94 | .94 |
|  | 2725 |  |  |  |  |  |  |  |  |  | .99 | .93 | .95 | .94 |
|  | 2997 |  |  |  |  |  |  |  |  |  |  | .98 | .95 | .96 |
|  | 3330 |  |  |  |  |  |  |  |  |  |  |  | .99 | .95 |
|  | 3747 |  |  |  |  |  |  |  |  |  |  |  |  | .99 |

I claim:

1. Apparatus for testing hearing, comprising a sound source for applying a sound to a subject's ear, and a sound detector for detecting the sound returned from the subject's inner ear in response to said sound, characterised in that said sound source produces a sequence of sounds constituting a maximum length sequence (MLS), a variant of such a sequence or a variant of a similar sequence.

2. Apparatus according to claim 1, wherein the sequence is a Legendre sequence, an M-pulse sequence or a De Bruijn sequence.

3. A method of testing hearing, wherein sound is applied to a subject's ear and the sound reflected from the subject's inner ear is detected, characterised in that the sound sequence constitutes a maximum length sequence (MLS), a variant of such a sequence or a variant of a similar sequence.

4. A method according to claim 3, wherein the sequence is a Legendre sequence, an M-pulse sequence or a De Bruijn sequence.

5. A method according to claim 3, wherein two sequences are used simultaneously.

6. A method according to claim 3, wherein two ears are tested simultaneously.

7. Apparatus for testing, hearing, comprising a sound source for applying to a subject's ear a sequence constituting a maximum length sequence (MLS), a variant of such a sequence or a variant of a similar sequence, a sound detector for detecting the sound responses returned from the subject's inner ear, the sequence of sounds being applied at a rate between sounds which is less than the durations of the sound responses, whereby the output of the detector is a waveform containing but not resembling the sequence of sound responses produced by the applied sequence of sounds, and an electronic means for recovering the sequence of sound responses from the waveform output from the detector.

8. Apparatus according to claim 7, wherein the electronic means acts to deconvolute the waveform output from the detector.

9. Apparatus according to claim 7, wherein the rate at which the sequence of sounds is applied to the subject's ear is greater than 50 sounds per second.

10. Apparatus according to claim 9, in which the rate is at least 500 sounds per second.

* * * * *